United States Patent
Szetsen

[11] Patent Number: 6,068,783
[45] Date of Patent: May 30, 2000

[54] IN-SITU AND NON-INTRUSIVE METHOD FOR MONITORING PLASMA ETCH CHAMBER CONDITION UTILIZING SPECTROSCOPIC TECHNIQUE

[75] Inventor: Steven Lee Szetsen, Hsinchu, Taiwan

[73] Assignee: Winbond Electronics Corp, Hsin Chu, Taiwan

[21] Appl. No.: 09/067,970

[22] Filed: Apr. 28, 1998

[51] Int. Cl.$^7$ ............................................. G01N 21/00
[52] U.S. Cl. ............................................. 216/60; 438/9
[58] Field of Search ................... 438/7, 8, 9, 14, 438/710, 714, 16; 216/59, 60

[56] References Cited

U.S. PATENT DOCUMENTS

| | | | |
|---|---|---|---|
| 4,493,745 | 1/1985 | Chen et al. | 156/626 |
| 4,609,426 | 9/1986 | Ogawa et al. | 156/626 |
| 5,211,825 | 5/1993 | Saito et al. | 156/643 X |
| 5,322,590 | 6/1994 | Koshimizu | 156/626 |
| 5,374,327 | 12/1994 | Imahashi et al. | 156/626 |
| 5,405,488 | 4/1995 | Dimitrelis et al. | 156/627 |
| 5,565,114 | 10/1996 | Saito et al. | 216/60 |
| 5,694,207 | 12/1997 | Hung et al. | 356/72 |
| 5,877,032 | 3/1999 | Guinn et al. | 216/60 X |
| 5,885,472 | 3/1999 | Miyazaki et al. | 216/60 |

*Primary Examiner*—Maria Nuzzolillo
*Assistant Examiner*—Susy Tsang
*Attorney, Agent, or Firm*—W. Wayne Liauh

[57] ABSTRACT

A spectroscopic method is disclosed to provide a non-intrusive and in-situ monitoring of plasma etching conditions during the fabrication of semiconductor devices using RF power. It includes the steps of: (a) selecting a single plasma gas as a probe, in a cleaned plasma etch chamber; (b) measuring the spectral intensities of the plasma gas; and (c) plotting the measured spectral intensities either directly or indirectly against the RF time. A single plasma gas is selected which exhibits opposite relationships with RF time at two respective wavelengths.

8 Claims, 3 Drawing Sheets

IN-SITU AND NON-INTRUSIVE METHOD FOR MONITORING PLASMA ETCH CHAMBER CONDITION UTILIZING SPECTROSCOPIC TECHNIQUE

FIELD OF THE INVENTION

The present invention relates to an improved plasma etching process with in-situ monitoring capability. More specifically, the present invention relates to a non-intrusive method for in-situ monitoring of the conditions in a plasma etching chamber. The method disclosed in the present invention is most advantageous in fabricating semiconductor devices wherein the plasma etching chamber contains plasma etching gases that can readily serve as in-situ monitoring probes and no foreign monitoring probes are required.

BACKGROUND OF THE INVENTION

Plasma etching is a process involving the selective removal of material by reactive free radicals or ions generated within a plasma. A plasma is an ionized gas in which concentrations of positive and negative ions are almost equal. The plasma may also contain free radicals which are electrically neutral yet highly reactive. Typically, a plasma is formed by introducing a predetermined gas into a plasma chamber and applying a radio frequency (RF) field to the plasma chamber. The gas introduced is chosen such that it will participate in the intended chemical reaction of a particular process. The RF field causes electron collisions with neutral or charged species to emit radiation. During the etching of semiconductor layer materials, halogen-containing compounds are commonly used in the gas phase as an etching gas.

One of the problems associated with the plasma etching process is that it is generally difficult to control. As a result, the plasma etching process must be continuously monitored to compensate for variations. For example, the etching chamber may be aged, and the etch time required for a freshly cleaned etching chamber will be different from that for an etching chamber that has been in use for some time. Thus, there often exist lot-to-lot variations in wafer attributes and characteristics. This may be minimized by diligent cleaning of the etching chamber. However, the high cleaning cost and the wasteful idled investment productivity dictate that the cleaning (and interruption) should be kept only at a level that is absolutely necessary. In order to balance these two opposite needs, an effective monitoring device is highly needed for the plasma etching process.

At the present time, the etcher chambers are typically monitored by checking the etching rate, particle count, etc. Sometimes, an "open chamber" procedure is utilized. All these procedures are wafer- and time-consuming. The open chamber procedure also causes highly undesirable interruptions in the manufacturing process. Furthermore, the open chamber condition is not the same as when it is in a vacuum.

U.S. Pat. No. 5,653,894 proposes a method which utilizes an active neural network to determine endpoint of a plasma etch process. At least two parameters, such as capacitance, voltage, current, power density, forward and reflected power and other signatures of the RF process are collected and processes using an active neural network to determine endpoint of the plasma etch process. The '894 patent teaches an improved method for analyzing collected parameters, but does not present any new approach as to how these parameters should be collected. The '894 patent also discloses monitoring the wavelength emitted from the wafers using an ellipsometer. However, it also reported that the wavelength used to obtain the ellopsometric traces varied from wafer to wafer and not every trace accurately indicated process endpoint.

U.S. Pat. No. 5,596,207 discloses a monitoring technique for quantifying the effect of plasma/etching during the formation of MOS transistors. The monitor employs a MOS capacitor comprising a thin oxide layer which separates a conductive plate from a semiconductive substrate. The capacitor is modified by placement of a conductive sidewall spacer of the same gate material around the periphery of the conductive plate. Electrical characterization is performed on the resulting modified MOS capacitor to yield information on peripheral damage.

U.S. Pat. No. 5,711,851 discloses a process for improving the performance of a temperature sensitive etch process. In the '851 patent, the temperature of a dry etch process of a semiconductor substrate in a plasma etch chamber is continuously monitored and controlled so as to maintain selectivity and high etch rate. The formation of plasma is terminated when the etching temperature exceeded a predetermined value, and resumed when it falls below another predetermined value.

U.S. Pat. No. 5,643,364 discloses an apparatus for plasma processing of semiconductor wafers or substrates which allows the use of a fixed RF match circuit at high RF frequencies by locating the RF power source at a distance substantially less than an eighth of a wavelength from the coupling device, which can be an electrode or antenna and which couples the RF power into a plasma chamber. The '364 patent also discloses an apparatus for detecting the endpoint of an etch or cleaning process by defecting when the reflected power or VSWR ceases to change as a function of the removal of the substance being etched or cleaned.

The above-mentioned inventions may have their advantages and disadvantages. However, because of the importance of monitoring the plasma etch chamber, especially with respect to the amount of expenses that can be saved and the problems that can be prevented, it is important to explore other, possibly better, monitoring techniques.

SUMMARY OF THE INVENTION

The primary object of the present invention is to develop a plasma etching method with improved in-situ monitoring capability. More specifically, the primary object of the present invention is to develop an improved non-intrusive and in-situ technique which can continuously monitor the conditions inside a plasma etch chamber, so as to ensure good quality of semiconductor devices fabricated inside the plasma etch chamber.

In the present invention, it was unexpectedly discovered that a conspicuously proportional relationship can be found between the emission spectral intensity of one or more plasma species and the RF time (RF time is the real time that has lapsed in the process of applying RF frequency to the gas in the plasma etching chamber) of the plasma etch chamber. Preferably, the spectral intensity of the plasma species is measured in the UV-visible wavelength range (about 200 nm–800 nm). Plasma species that have been found to exert such conspicuous proportional relationship with RF time include F, CF, $CF_2$, $CF_3$, CO, O. Any of these plasma species can be used as a probe to monitor the conditions of a plasma etch chamber. However, in order to minimize fluctuations and improve accuracy and reproducibity, it is highly preferred that the monitoring process utilize at least a pair of probes, and use their ratio to report the monitored result. Also, it is preferably that more than one pair of such probes be utilized. The preferred pairs of probes include the [$CF_2$]/[F] pair or two characteristic excited states of the CO plasma gas.

One of the main advantages of the method disclosed in the present invention is that it is non-intrusive and is performed in-situ. The plasma spectroscopic technique required in the monitoring process can be either absorption type or emission type. Both are in-situ and non-intrusive. Absorption type requires external light source; whereas, the light source of emission type comes from the molecule itself. During the plasma etching process, the etching molecules are pumped to very highly excited states. Typically, the excited molecules return to their ground states by emitting photons. By measuring the population of the photons (i.e., the spectral intensity) at a specific wavelength, the inner condition of a plasma etching chamber can be monitored. By using the ratio of one or more pairs of plasma probes, the accuracy of the technique can be maintained at a level required for production runs.

BRIEF DESCRIPTION OF THE DRAWING

The present invention will be described in detail with reference to the drawing showing the preferred embodiment of the present invention, wherein.

DETAILED DESCRIPTION OF THE PREFERRED EMBODIMENT

The present invention discloses an improved non-intrusive and in-situ technique which can continuously monitor the conditions inside a plasma etch chamber, so as to ensure good quality of semiconductor devices to be fabricated inside the plasma etch chamber.

Prior art methods have taught the use of using temperature, capacitance, voltage, current, power density, forward and reflected power, etc., for monitoring the progress of a plasma etching process. In the present invention, it was unexpectedly discovered that a conspicuously proportional relationship can be found between the emission spectral intensity of one or more plasma species and the RF time of the plasma etching chamber. The spectral intensity of the plasma species is preferably measured in the UV-visible range, between about 200 nm and about 800 nm. It was found in the present invention that plasma species such as F, CF, $CF_2$, $CF_3$, CO, O, etc., can exhibit a conspicuous proportional relationship with the RF time. Any of these plasma species can be used as a probe to monitor the conditions of a plasma etch chamber. However, in order to minimize fluctuations and improve the measurement accuracy, the monitoring process should be done which utilizes at least one pair of probes, and use their ratio to report the monitored result. It is also possible that more than one pair of such probes can be utilized.

As discussed above, one of the main advantages of the method disclosed in the present invention is that it is non-intrusive and is performed in-situ. The plasma spectroscopic technique required in the monitoring process can be either absorption type or emission type. Both are in-situ and non-intrusive. Absorption type requires external light source. Whereas, the light source of emission type comes from the molecule itself. During the plasma etching process, the etching molecules are pumped to very highly excited states. Typically, the excited molecules return to their ground states by emitting photons. By measuring the population of the photons (i.e., the spectral intensity) at a specific wavelength, the inner condition of a plasma etching chamber can be monitored. By using the ratio of one or more pairs of plasma probes, the accuracy of the technique can be maintained at a level required for production runs.

Figure 1:
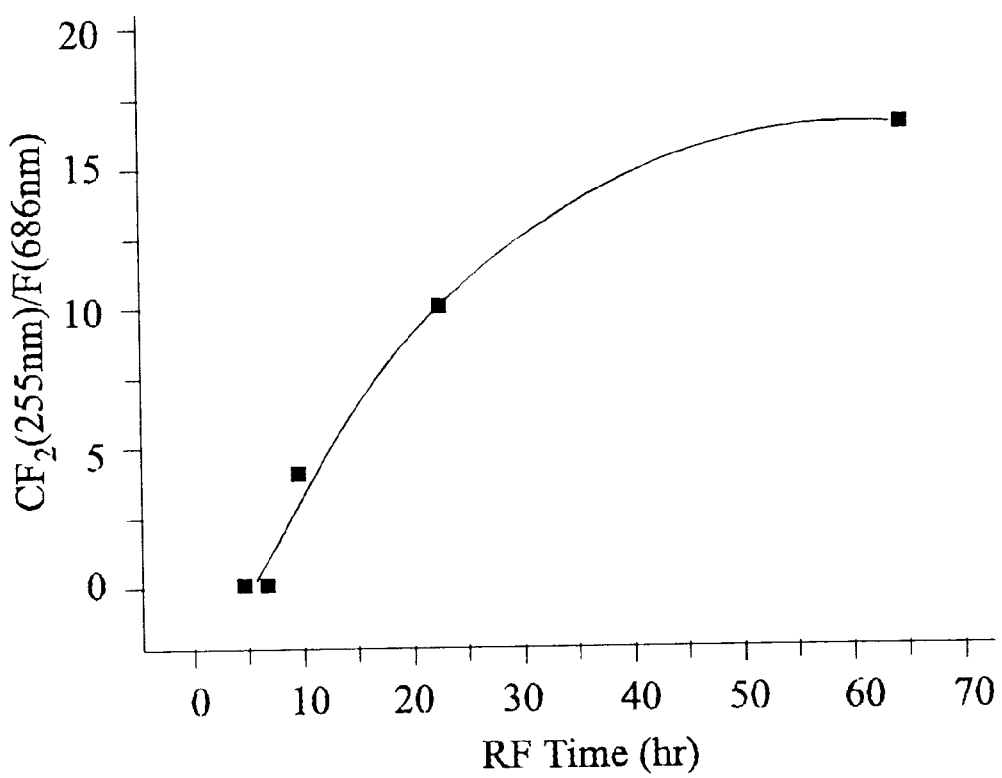
FIG. 1 is a schematic drawing of the non-intrusive in-situ technique for monitoring the inside conditions of a plasma etching chamber.

Now referring to the drawings, wherein FIG. 1 show a schematic drawing of a preferred embodiment of apparatus to implement the non-intrusive in-situ technique disclosed in the present invention for monitoring the inside conditions of a plasma etching chamber. FIG. 1 shows a plasma etching chamber 1, a monochromator 2, an optical fiber 3 connecting between the plasma etching chamber 1 and the monochromator. Gases that are typically used in the plasma etching of dielectric materials include $CHF_3$, $CF_4$, $C_4F_8$, etc., and sometimes with the addition of CO and $O_2$. Light emission from the plasma etching chamber 1 is collected into the monochromator 2 via the optical fiber 3. A photosensitive photodiode 4 is placed at the end of the monochromator 2 to tranform the collected photon into electrical signals. The electrical signals are then processed by a computer 5. By adjusting the grating angle inside the monochromator 2, spectral intensity of different wavelength can be analyzed. The simplicity of FIG. 1 also manifests another very important advantage of the present invention in that a very simple and cost-effective method is developed in the present invention to allow very valuable information to be collected which will greatly improve the plasma etching process.

The present invention will now be described more specifically with reference to the following examples. It is to be noted that the following descriptions of examples, including the preferred embodiment of this invention, are presented herein for purposes of illustration and description, and are not intended to be exhaustive or to limit the invention to the precise form disclosed.

EXAMPLE 1

Figure 2:
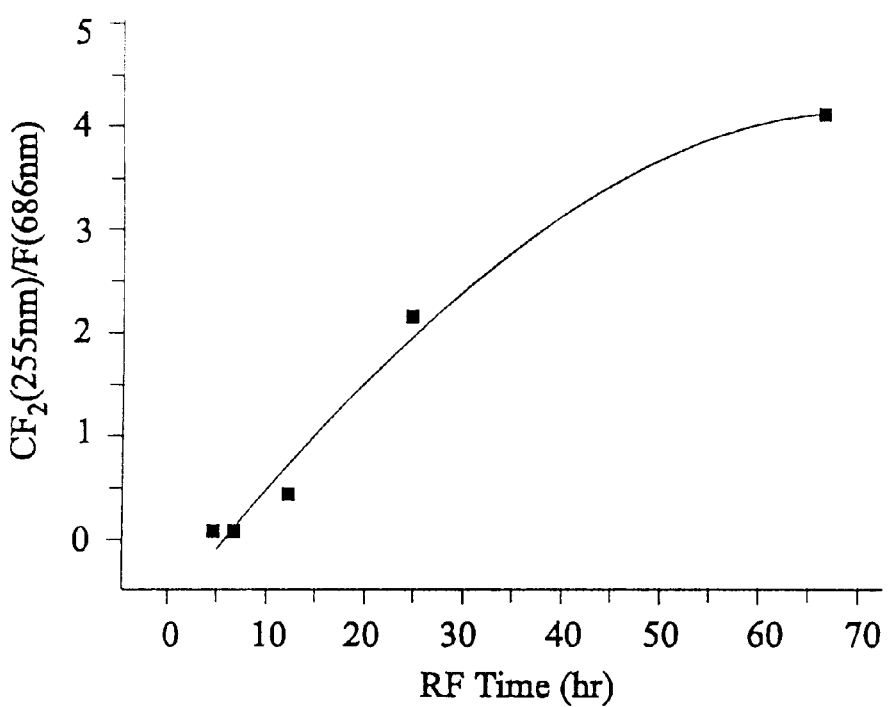
FIG. 2 is a plot of the ratio of the spectra intensities of the [$CF_2$]/[F] pair of probes as a function of RF time for Example 1.

A dielectric layer was etched in a freshly cleaned plasma etching chamber which contained $C_4F_8$:$O_2$:Ar=5:1:20, at a pressure of 50 mTorr. The spectral intensities at spectral lines of 686 nm and 255 nm, which corresponded to plasma species F ($3s^4P_3 \rightarrow 3p^4P_3$) and $CF_2$ ($A^1B_1(v'=4) \rightarrow X^1A_1(v''=0)$), respectively, were measured. FIG. 2 is a plot of the ratio of the spectra intensities of the [$CF_2$]/[F] pair of probes as a function of RF time for Example 1. The same data shown in FIG. 2 are also listed in Table 1, below.

TABLE 1

| RF Time | 4.5 hr | 6.5 hr | 12 hr | 24 hr | 67 hr |
|---|---|---|---|---|---|
| [$CF_2$]/[F] | 0..028 | 0.032 | 4.550 | 9.204 | 16.536 |

As shown in FIG. 2, a very clear proportional relationship can be found to exist. This curve can be utilized as a reference in monitoring other plasma etching processes under a similar recipe.

Figure 3:
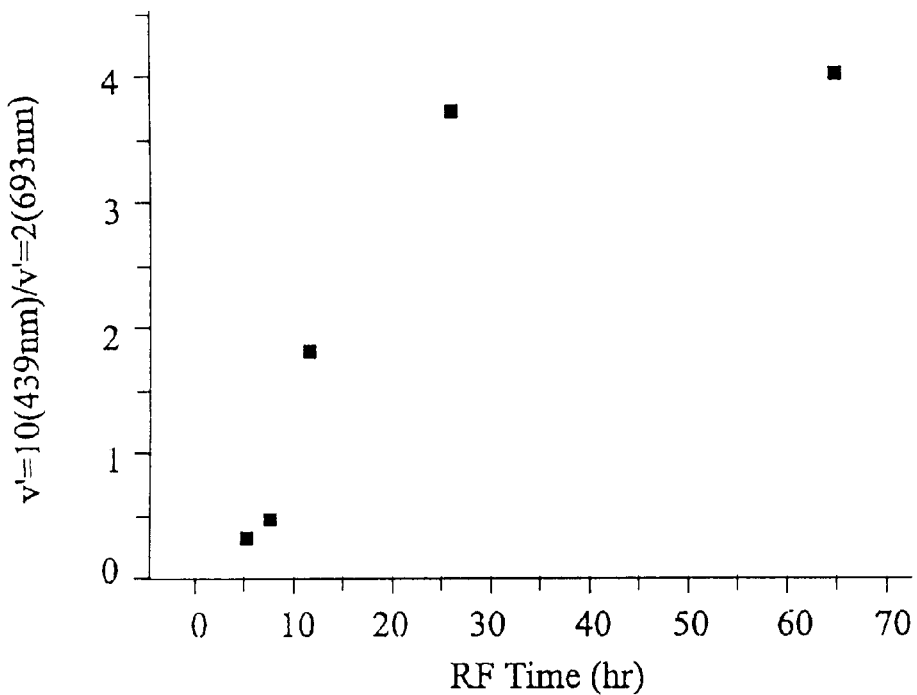
FIG. 3 is a plot of the ratio of the spectra intensities of CO probe at wavelengths of 439 nm and 693 nm, as a function of RF time for Example 1.

FIG. 3 is a plot of the ratio of the spectra intensities of CO probe at wavelengths of 439 nm (corresponding to $d^3\pi(v'=10)$) and 693 nm (corresponding to $a^3\pi(v'=2)$), as a function of RF time for Example 1. Again, a very clear proportional relationship can be found to exist. This curve can also be utilized as another reference in monitoring other plasma etching processes under a similar recipe.

EXAMPLE 2

Figure 4:
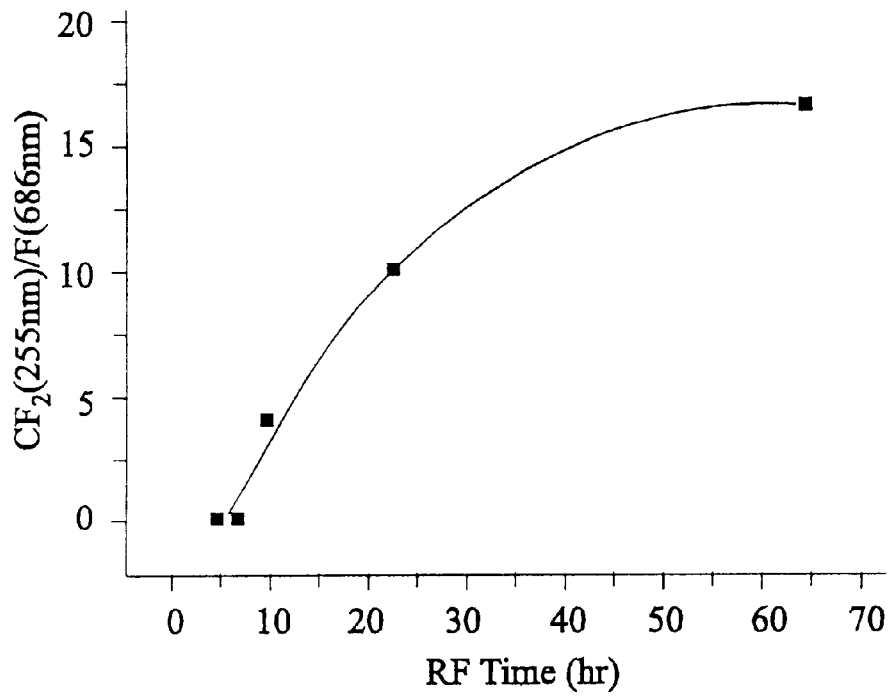
FIG. 4 is a plot of the ratio of the spectra intensities of the [$CF_2$]/[F] pair of probes as a function of RF time for Example 2.

A dielectric layer was etched in a freshly cleaned plasma etching chamber which contained $C_4F_8:CO:Ar=1:2.2:21$, at a pressure of 40 mTorr. The spectral intensities at spectral lines of 686 nm and 255 nm, which corresponded to plasma species F ($3s^4P_3 \rightarrow 3p^4P_3$) and $CF_2$ ($A^1B_1(v'=4) \rightarrow X^1A_1(v''=0)$), respectively, were measured. FIG. 4 is a plot of the ratio of the spectra intensities of the $[CF_2]/[F]$ pair of probes as a function of RF time for Example 2. The same data shown in FIG. 4 are also listed in Table 2, below.

TABLE 2

| RF Time | 4.5 hr | 6.5 hr | 12 hr | 24 hr | 67 hr |
|---|---|---|---|---|---|
| $[CF_2]/[F]$ | 0.016 | 0..027 | 0.380 | 2.229 | 4.212 |

Again, a very clear proportional relationship can be found to exist. This curve can be utilized as a reference in monitoring other plasma etching processes under a similar recipe.

Figure 5:
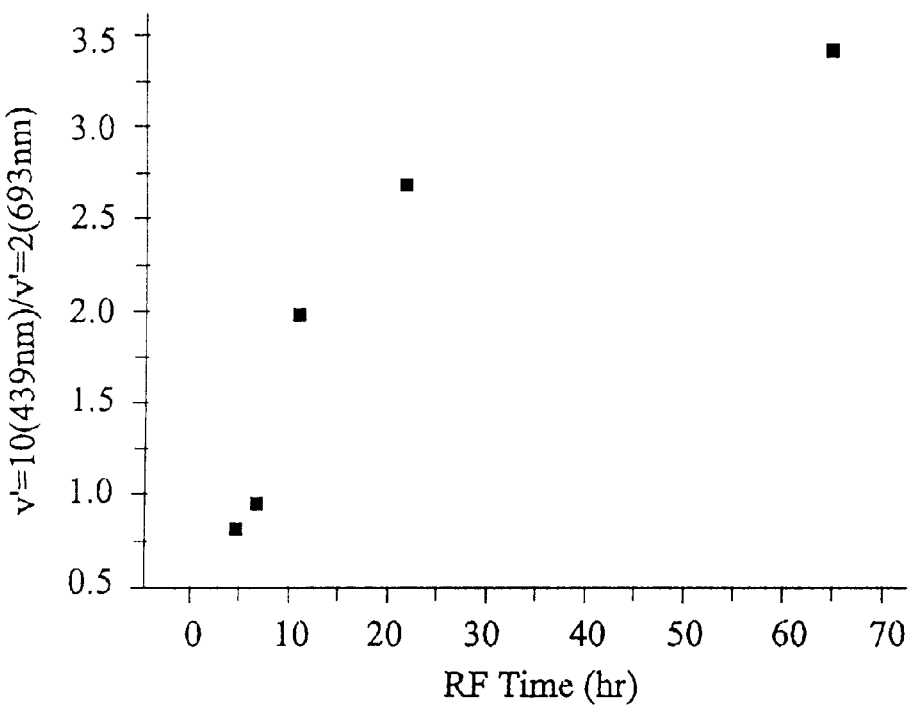
FIG. 5 is a plot of the ratio of the spectra intensities of CO probe at wavelengths of 439 nm and 693 nm, as a function of RF time for Example 2.

FIG. 5 is a plot of the ratio of the spectra intensities of CO probe at wavelengths of 439 nm (corresponding to $d^3\pi(v'=10)$) and 693 nm (corresponding to $a^3\pi(v'=2)$), as a function of RF time for Example 2. Again, a very clear proportional relationship can be found to exist. This curve can also be utilized as another reference in monitoring other plasma etching processes under a similar recipe.

The proportional relationship between the spectral intensity ratio of the $[CF_2]/[F]$ pair and the RF time can be explained by the deposition of polymer molecules on the chamber wall. A major constituent of the deposited polymer is —$(C_xF_y)$—, a fluorocarbon polymer. $CF_2$ is one of the precursors of polymerization. Thus, at relatively small RF times, i.e., when the etching chamber is clean, most of the $CF_2$ molecules produced during the discharge will collide with the chamber wall, which typically comprises anodized aluminum, to form the fluorocarbon polymer. This is reflected in the low spectral intensity ratio of the $[CF_2]/[F]$ pair. As the RF time increases, the chamber wall is increasingly coated with a layer of flourocarbon polymer, which is inert to reaction with $CF_2$. Thus, the concentration of $CF_2$ in the etching chamber will increase. On comparison, the concentration of F was not affected by the chamber wall condition, and the abstraction reaction involving F remained significant such that its emission spectral intensity would decrease with RF time. As a result, spectral intensity ratio of the $[CF_2]/[F]$ pair increased with RF time, as shown in FIGS. 2 and 4.

With respect to the proportional relationship between the ratio of the spectra intensities of the CO probe at (v'=10) and (v'=2), it is also believed that this relationship is related to the deposition of polymer on the chamber wall. When the CO molecule collides with the wall surface, it tends to relax from a high vibrational state to a lower one. Depending on the surface which provides the collision, the relaxation rates may be different. For example, a metal (e.g., aluminum) surface will have a higher rate than the polymer-coated (e.g., a fluorocarbon polymer-coated) surface. Therefore, at short RF times, i.e., when the etch chamber is clean, most of the high vibrational states of the CO molecule will relax to low states. On the other hand, at long RF times, i.e., when the chamber is coated with a polymer layer, an appreciable amount of CO will remain at high vibrational state, resulting in an increased ratio between spectra intensities of CO at 439 nm (v'=10) and at 693 nm (v'=2).

One of the key elements contributing to the success of the present invention is the proper selection of the plasma probe. Preferably a pair of plasma gases, as in the above example of $[CF_2]/[F]$ pair, or a single plasma gas but at two characteristic wavelengths, as in the above example of CO at 439 nm (v'=10) and at 693 nm (v'=2), is selected and their ratio is calculated to either eliminate noise or magnify the measured result. Furthermore, while it was speculated that the changes in the chamber wall condition may be the reason for the changes in the spectral intensity, the present invention is not limited to monitoring chamber wall conditions. Any condition that will cause a change in the spectral intensity in one or more of the probe plasma gases can be monitored with the method disclosed in the present invention.

The foregoing description of the preferred embodiments of this invention has been presented for purposes of illustration and description. Obvious modifications or variations are possible in light of the above teaching. The embodiments were chosen and described to provide the best illustration of the principles of this invention and its practical application to thereby enable those skilled in the art to utilize the invention in various embodiments and with various modifications as are suited to the particular use contemplated. All such modifications and variations are within the scope of the present invention as determined by the appended claims when interpreted in accordance with the breadth to which they are fairly, legally, and equitably entitled.

The method for monitoring the etching conditions of the plasma etching chamber can further include the steps of selecting a reference wavelength whose spectral intensity remains relatively constant with respect to RF time, and measuring the spectral intensity at the reference wavelength as a reference intensity. Then a ratio of the spectral intensities of the probe and the reference wavelength is plotted against the RF time.

What is claimed is:

1. A method for monitoring etching conditions in a plasma etch chamber comprising the steps of:
   (a) selecting a single plasma gas as a probe; and
   (b) measuring a spectral intensity of said plasma gas at a pair of predetermined wavelengths; wherein
      (i) said pair of wavelengths are selected such that the spectral intensity at one wavelength will increase with RF time and the spectral intensity at another wavelength will decrease with RF time; and
      (ii) the etching conditions are monitored by plotting a ratio of the spectral intensities at said pair of wavelengths against said RF time.

2. The method for monitoring etching conditions in a plasma etch chamber according to claim 1 wherein said single plasma gas is CO.

3. The method for monitoring etching conditions in a plasma etch chamber according to claim 2 wherein said pair of wavelengths are 439 nm and 693 nm, corresponding to the energy states of CO at $d^3\pi(v\pi=10)$ and $a^3\pi(v'=2)$, respectively.

4. The method for monitoring etching conditions in a plasma etch chamber according to claim 1 which further comprises the steps of:

(a) selecting a reference wavelength whose spectral intensity remains relatively constant with respect to RF time, and measuring the spectral intensity at said reference wavelength as a reference intensity; and (b) plotting a ratio of the spectral intensities of said probe and said reference wavelength against said RF time.

5. A plasma etching and monitoring method for etching semiconductor wafers or substrates, comprising the steps of:

(a) obtaining a plasma etching chamber connected to a spectral intensity measuring and analyzing means via an optical conduit;

(b) introducing a plurality of plasma gases into said plasma etching chamber;

(c) selecting a single plasma gas as a probe;

(d) proceeding a plasma etching process using an RF power source; and (e) measuring a spectral intensity of said single plasma gas at a pair of predetermined wavelengths; wherein (i) said pair of wavelengths are selected such that the spectral intensity at one wavelength will increase with RF time and the spectral intensity at another wavelength will decrease with RF time; and (ii) the etching condition of said plasma etch chamber is monitored by plotting a ratio of the spectral intensities at said pair of wavelengths against said RF time.

6. The plasma etching and monitoring method according to claim 5 wherein said single plasma gas is CO.

7. The plasma etching and monitoring method according to claim 6 wherein said pair of wavelengths are 439 nm and 693 nm, corresponding to the energy states of CO at $d^3\pi(v'=10)$ and $a^3\pi(v'=2)$, respectively.

8. The plasma etching and monitoring method according to claim 5 which further comprises the steps of:

(a) selecting a reference wavelength whose spectral intensity remains relatively constant with respect to RF time, and measuring the spectral intensity at said reference wavelength as a reference intensity; and (b) plotting a ratio of the spectral intensities of said probe and said reference wavelength against said RF time.

* * * * *